United States Patent [19]

Mitrovic

[11] 4,000,300

[45] Dec. 28, 1976

[54] CONTROL AND PREVENTION OF BLACKHEAD DISEASE IN BIRDS

[75] Inventor: Milan Mitrovic, Nutley, N.J.

[73] Assignee: Hoffmann-La Roche Inc., Nutley, N.J.

[22] Filed: Jan. 26, 1976

[21] Appl. No.: 651,361

Related U.S. Application Data

[63] Continuation-in-part of Ser. No. 552,483, Feb. 24, 1975, abandoned.

[52] U.S. Cl. .............................................. 424/273
[51] Int. Cl.[2] ...................................... A61K 31/415
[58] Field of Search ................................... 424/273

[56] References Cited

OTHER PUBLICATIONS

Dransch et al.—Chem. Abst., vol. 81 (1974), p. 13512r.
Beard et al.—Chem. Abst., vol. 82 (1975), p. 156,301c.

*Primary Examiner*—Sam Rosen
*Attorney, Agent, or Firm*—Samuel L. Welt; Bernard S. Leon; Gerald S. Rosen

[57] ABSTRACT

Novel compositions containing a 2-carbalkoxy-amino-benzimidazole-5(6)-phenyl ether, useful for the control and prevention of blackhead disease in birds.

12 Claims, No Drawings

CONTROL AND PREVENTION OF BLACKHEAD DISEASE IN BIRDS

RELATED APPLICATIONS

This is a continuation-in-part of U.S. Patent Application Ser. No. 552,483 filed Feb. 24, 1975, now abandoned, the benefit of the priority date of which is claimed herein.

SUMMARY OF THE INVENTION

This invention relates to veterinary compositions and to their use in the control and prevention of blackhead disease in birds. More specifically, this invention relates to the method of treatment of birds, particularly poultry, with certain 2-carbalkoxy-amino-benzimidazole-5(6)-phenyl ethers for preventing and controlling blackhead disease.

BACKGROUND OF THE INVENTION

Blackhead disease, invariably fatal, occurs in birds of all ages. Its economic impact in terms of losses is greatest in turkeys, which are particularly susceptible to the disease. Other poultry and birds, e.g., chickens, guineas, quails, pheasants and pea-fowl, also frequently contract the disease which is caused by a flagellate protozoan identified as *Histomonas meleagridis*. Its clinical symptoms are manifested by lesions and inflammation of the ceca and liver. Because of its etiology and gross pathology, the disease is known as histomoniasis and/or infectious enterohepatitis.

*Histomonas meleagridis* is mostly harbored by the common poultry cecal worms, *Heterakis gallinarum*, and its eggs, in which it is able to live for extended periods. This source is mainly responsible for the transmission of the disease.

The disease is contracted orally by the birds when consuming feed or water contaminated with droppings containing the infectious organism or by swallowing cecal worms or their eggs harboring the parasite. The incubation period of blackhead is about 14 to 21 days. The disease manifests itself in the infected birds by inappetence, a constant yellowish or sulfur colored diarrhea and weight loss followed by death. Generally, yound birds are more susceptible than adults, although the mortality rate in both groups is very high. Adult birds are usually sick for several days losing much weight before they die while the yound birds succumb much quicker.

Post-mortem examinations of the birds disclose multiple lesions and ulcerations of the cecal wall and liver. The ceca are filled with yellowish-green cores and the cecal walls are thickened. The lesions of the liver consist of large irregular reddened or gray necrotic areas.

In turkeys particularly, the prognosis of the disease is poor. The high mortality rate, at times 100% of the flock, results in large losses to the poultry breeder. Losses are in excess of $4 million annually. Heaviest losses are during the first three months of life, however, other age groups are also affected. The disease is prevalent in all areas where turkeys are raised.

The prevention and control of blackhead disease is at present effected by various chemotherapeutic agents such as arsenicals, nitrothiazoles, nitrofurans and nitroimidazoles.

This invention provides histomonostat compositions containing certain 2-carbalkoxy-amino-benzimidazole-5(6)-phenyl esters for combatting blackhead disease by preventing and curing the disease and which not only possess a high degree of efficacy with negligible side effects at low dosages but also do not suppress the weight gain of the treated infected birds.

DETAILED DESCRIPTION OF THE INVENTION

The objects of this invention are accomplished when birds, particularly turkeys, though the invention is not limited thereto, are treated with compositions containing from about 0.003125 to 0.0125% by weight of the active compounds. Generally from 0.003125 gram to 0.0125 gram per hundred grams of feed or water or other inert carrier of the active compound, hereinafter defined, is used in treating the birds. Generally, when the inert carrier is dry feed, from 0.00625 gram to 0.0250 gram of active compound per hundred grams of feed is used and when the inert carrier is water, from 0.003125 gram to 0.0125 gram of active compound per 100 cc. of water is used. This treatment results in substantially complete prevention and control of the disease. The particular dosage depends upon the specific composition used and the method of administration. The preferred method of treatment is by oral administration, e.g., in the feed, in the drinking water, or in other ingestable inert carriers. Generally, a bird will take in, on a weight basis, about twice as much water as dry feed. Thus, the dosage of histomonostat in water is about half that in the feed. The preferred preventive dosage in feed is about 0.00625 gram per 100 grams of feed. In drinking water the preferred preventive dosage is about 0.003125 gram per 100 cc. of water. For therapy, usually twice the preventive dosage is used. The amount of active compound which an individual bird ingests depends on the amount of feed or water ingested. This varies with the individual bird. Usually, about 3 mg./kg. for older birds and about 6 mg./kg. for younger birds of active compound per day are ingested when the birds are allowed free access to the feed and half these amounts when allowed free access to drinking water.

The compounds useful in the compositions of this invention for combatting blackhead disease, particularly in turkeys, are 2-carbalkoxy-amino-benzimidazole5(6)-phenyl ethers represented by the formula

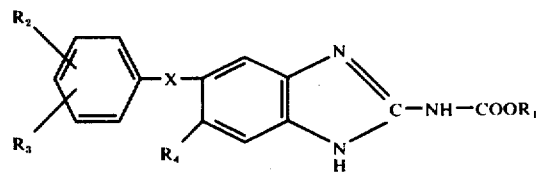

wherein R₁ is alkyl having from 1 to 4 carbon atoms, R₂ and R₃, which may be the same or different, each are hydrogen, hydroxy, alkoxy having from 1 to 4 carbon atoms, halogen, trifluoromethyl, alkyl having from 1 to 4 carbon atoms or carbalkoxy having from 1 to 4 carbon atoms in the alkoxy group, R₄ is hydrogen or chlorine and X is oxygen or sulfur.

Compositions containing active compounds represented by formula I in which R₁ is methyl, R₂, R₃ and R₄ each are hydrogen and X is oxygen or sulfur are especially preferred.

The alkyl groups of R₁, R₂ and R₃ are lower alkyl of 1 to 4 carbon atoms, e.g., methyl, ethyl, propyl, isopropyl, butyl and tert. butyl The alkoxy groups of $R_2$ and $R_3$ are lower alkoxy of 1 to 4 carbon atoms, e.g., methoxy, ethoxy, propoxy, isopropoxy and butoxy. Halogen of $R_2$ and $R_3$ is fluorine, chlorine, bromine and iodine. The carbalkoxy groups of $R_2$ and $R_3$ are lower carbalkoxy of 1 to 4 carbon atoms in the alkoxy group, e.g., carbomethoxy, carbopropoxy and carbobutoxy.

The compounds useful as active ingredients in this invention are disclosed, e.g., in the British Patent Specification No. 1,360,180 and in Chemical Abstracts, Vol. 81, page 12514 (13512r) (1974).

Most preferred of the active compounds within the scope of formula I is methyl-5-(phenylthio)-2-benzimidazolecarbamate represented by the formula:

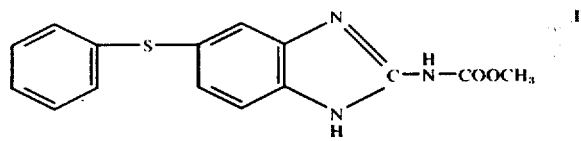

This compound (herein referred to as Compound A) is an almost colorless powder melting at 233° C with decomposition. It is soluble in dimethylsulfoxide. It is also known as fenbendazole.

Further examples of preferred active compounds within the scope of formula I are:

Methyl-5-(4-methyl-phenylthio)-2-benzimidazolecarbamate (Compound B),
Methyl-5-(3-methyl-phenylthio)-2-benzimidazolecarbamate (Compound C),
Methyl-5-(4-chloro-phenylthio)-2-benzimidazolecarbamate (Compound D).

Other active compounds within the scope of formula I are specifically referred to in British Patent Specification No. 1,360,180.

In the preferred embodiment of this invention, the compositions are administered orally ad libitum to birds susceptible to blackhead disease or infected with blackhead disease. The compositions can be formulated by incorporating the active compound into conventional pharmaceutical carrier materials, either organic or inorganic, which are suitable for oral application and can be formulated with other non-interfering therapeutically useful materials. The preferred mode of administration of the drug is simple admixture with the feed or suspended in drinking water.

The effectiveness of the active compounds within the scope of formula I against *H. meleagridis* and as promoting the growth and feed conversion of the birds is illustrated in the following manner:

Two week old white turkey poults were used throughout the experiments. Four birds selected according to weight and sex (50% female and 50% male) were used in each group, an open-formula, custom-mix turkey prestarter mash, composed of natural feedstuffs and supplemented with minerals and vitamins but free from additives such as medicaments was used as the basal ration. The test compound was added to the basal ration in various amounts to obtain the desired concentration. The medicated feed was given three days in advance of infection and for 21 consecutive days post-infection. The infection was standardized by administering to each turkey orally 500 *H. gallinarum* embryonated eggs containing *H. meleagridis*. For each test, parallel sets of uninfected, unmedicated controls (UUC) and infected, unmedicated controls (IUC) were used.

Treatment is conducted by placing the feed and/or drinking water containing the active compound before the birds for ingestion ad libitum. For example, in the case of poults, 0.00625 gram of a compound within the scope of formula I is mixed with each 100 grams of poultry feed and put into feeding area.

At the termination of each experiment, the surviving birds were sacrificed, autopsied and scored for gross pathological lesions of the liver and ceca, if any, and their intensity. The degree of pathology is scored from 0 (no lesions) to 5 (death) and averaged for each group of test birds. This is called the average degree of infection (ADI). Weight gain, daily feed intake, feed efficiency, morbidity, and mortality were recorded. The parameters of the test compound's activity were expressed as minimal effective dose (MED), i.e., lowest percent by weight in feed at which it is active. A compound is considered active if at the concentration tested it (a) prevented mortality; (b) prevented or reduced pathology (ADI 0 to 1.0) and (c) did not suppress the weight gain of the medicated birds below 90% of the control birds on the same basal ration which is unmedicated.

The following are the results of the tests, Table I exhibiting the results of an initial screening test with the four compounds referred to above as Compounds A, B, C and D, Table II referring to the results of a test carried out with compound A (fenbendazole) in order to titrate the MED of this compound.

TABLE I

| | Initial Screening Test | | | | |
|---|---|---|---|---|---|
| Group | Conc. in Feed % by Weight | No. of Birds | Weight Gain % of Control | Mortality % | ADI |
| UUC | 0 | 4 | 100 | 0 | 0.0 |
| IUC | 0 | 4 | 68.6 | 50 | 4.8 |
| Compound A | 0.00625 | 4 | 100 | 0 | 0.0 |
| Compound B | 0.00625 | 4 | 100 | 0 | 0.0 |
| Compound C | 0.00625 | 4 | 97.6 | 0 | 0.0 |
| Compound D | 0.00625 | 4 | 110.3 | 0 | 0.0 |

TABLE II

| | Titration to MED | | | | | |
|---|---|---|---|---|---|---|
| Group | Conc. in Feed % by Weight | No. of Birds 4 Birds (Duplicate) | Weight Gain % of Control | Feed Conversion | Mortality % | ADI |
| UUC | 0 | 8 | 100 | 1.76 | 0 | 0.0 |

TABLE II-continued

| Group | Conc. in Feed % by Weight | No. of Birds 4 Birds (Duplicate) | Weight Gain % of Control | Feed Conversion | Mortality % | ADI |
|---|---|---|---|---|---|---|
| IUC | 0 | 8 | 60 | 4.34 | 62.5 | 4.2 |
| Compound A | 0.0125 | 8 | 102 | 1.73 | 0 | 0.0 |
| | 0.00625 | 8 | 100 | 1.73 | 0 | 0.0 |
| | 0.003125 | 8 | 99 | 1.78 | 0 | 0.0 |
| | 0.00156 | 8 | 69 | 3.82 | 50 | 3.2 |

The data in Tables I and II show that compounds A, B, C and D exhibited a high degree of activity at a concentration of 0.00625% (Table I) and that fenbendazole (Compound A) exhibited a high degree of activity at concentration of 0.0125 to 0.003125% by weight in feed. At these concentrations fenbendazole prevented mortality and morbidity, and allowed improved weight gain and feed efficiency. The active compound is effective in dosages as low as 0.003125% in feed.

The active compounds can be prepared as a premix or feed supplement containing from about 1 to about 90% by weight of the premix formulation which can also contain carriers of diluents such as corn meal, germ meal, lactose, corn starch, talc, gelatin, magnesium stearate, oyster shell flour, calcium silicate and the like. Other compatible medicaments may also be added to the premix. The premix can be added to commercial feed and intimately mixed therewith to obtain uniform distribution yielding an effective concentration level of the active compound for preventive and therapeutic use as well as for increasing feed efficiency and promoting growth. The feed supplement or premix can be readily mixed with the turkey ration by any conventional technique for mixing feeds.

EXAMPLE I

The following example illustrates a typical feed supplement formulation of a 12½% premix for use:

| | Grams/Kilo |
|---|---|
| Fenbendazole (Compound A) | 125.0 |
| Pulverized Oyster Shell Flour | 825.0 |
| Microcel E (Calcium Silicate) | 50.0 |
| & Total Weight Grams | 1000.0 |

Procedure

1. The pulverized oyster shell flour was placed in a suitable mixer and while mixing, the Microcel E was slowly added and thoroughly mixed.
2. While mixing continuously, the fenbendazole was slowly added and mixed until the mixture was homogeneous.
3. The premix was then added to a commercial poultry feed at the ratio of one pound/ton to yield a concentration of 0.00625% fenbendazole and thoroughly mixed.
4. This medicated feed was used in the mash form and it can also be pelleted.

Amounts of the above premix may be added to the commercial feed to yield medicated levels ranging from 0.003125 to 0.0125% or more. The commerical feeds to which the premix is added may be free of other medicaments or may contain other medicaments if the final mixture is compatible.

I claim:

1. A composition for the control and prevention of blackhead disease in birds comprising poultry feed or drinking water containing, as the active compound, about 0.003125 to about 0.0125% by weight of a compound represented by the formula

wherein $R_1$ is alkyl having from 1 to 4 carbon atoms, $R_2$ and $R_3$, which may be the same or different, each are hydrogen, hydroxy, alkoxy having from 1 to 4 carbon atoms, halogen, trifluoromethyl, alkyl having from 1 to 4 carbon atoms or carbalkoxy having from 1 to 4 carbon atoms in the alkoxy group, $R_4$ is hydrogen or chlorine and X is oxygen or sulfur.

2. A composition according to claim 1 wherein methyl-5-(phenylthio)-2-benzimidazolecarbamate is the active compound.

3. A composition according to claim 1 wherein methyl-5-(4-methylphenylthio)-2-benzimidazolecarbamate is the active compound.

4. A composition according to claim 1 wherein methyl-5-(3-methylphenylthio)-2-benzimidazolecarbamate is the active compound.

5. A composition according to claim 1 wherein methyl-5-(4-chlorophenylthio)-2-benzimidazolecarbamate is the active compound.

6. A method of combatting blackhead disease in birds in need of such treatment, which comprises orally administering ad libitum to said birds poultry feed or drinking water containing an anti-histomonal effective amount of, as the active compound, a compound represented by the formula

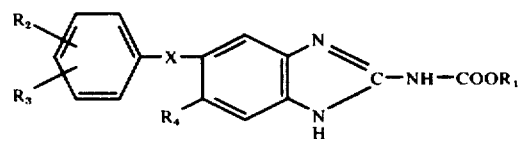

wherein $R_1$ is alkyl having from 1 to 4 carbon atoms, $R_2$ and $R_3$, which may be the same or different, each are hydrogen, hydroxy, alkoxy having from 1 to 4 carbon atoms, halogen, trifluoromethyl, alkyl having from 1 to 4 carbon atoms or carbalkoxy having from 1 to 4 carbon atoms in the alkoxy group, $R_4$ is hydrogen or chlorine and X is oxygen or sulfur.

7. A method of claim 6 wherein said composition contains as the active compound, methyl-5-(phenylthio)-2-benzimidazolecarbamate.

8. A method of claim 6 wherein said composition contains as the active compound, methyl-5-(4-methylphenylthio)-2-benzimidazolecarbamate.

9. A method of claim 6 wherein said composition contains as the active compound, methyl-5-(3-methylphenylthio)-2-benzimidazolecarbamate.

10. A method of claim 6 wherein said composition contains as the active compound, methyl-5-(4-chlorophenylthio)-2-benzimidazolecarbamate.

11. The method of claim 6 wherein said composition contains from about 0.003125 to about 0.0125% by weight of active compound.

12. A method of promoting growth and increasing feed efficiency in birds suffering from blackhead disease, which comprises orally administering ad libitum to said birds a poultry feed containing a growth promoting and feed efficiency increasing amount of a composition containing as the active compound a compound represented by the formula

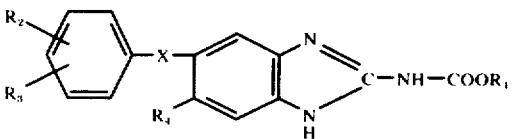

wherein $R_1$ is alkyl having from 1 to 4 carbon atoms, $R_2$ and $R_3$, which may be the same or different, each are hydrogen, hydroxy, alkoxy having from 1 to 4 carbon atoms, halogen, trifluoromethyl, alkyl having from 1 to 4 carbon atoms or carbalkoxy having from 1 to 4 carbon atoms in the alkoxy group, $R_4$ is hydrogen or chlorine and X is oxygen or sulfur.

* * * * *